(12) United States Patent
Rathjen

(10) Patent No.: US 6,746,400 B2
(45) Date of Patent: Jun. 8, 2004

(54) DEVICES AND METHODS FOR DETERMINING THE INNER PRESSURE OF AN EYE

(75) Inventor: Christian Rathjen, Bremen (DE)

(73) Assignee: SIS AG Surgical Instrument Systems, Brugg (CH)

( * ) Notice: Subject to any disclaimer, the term of this patent is extended or adjusted under 35 U.S.C. 154(b) by 47 days.

(21) Appl. No.: 10/023,646

(22) Filed: Dec. 21, 2001

(65) Prior Publication Data

US 2002/0193675 A1 Dec. 19, 2002

(30) Foreign Application Priority Data

Jun. 13, 2001 (WO) .............................. PCT/CH01/00366

(51) Int. Cl.$^7$ ................................................ A61B 3/16
(52) U.S. Cl. ...................................... 600/405; 600/399
(58) Field of Search .............................. 600/398, 399, 600/405, 561

(56) References Cited

U.S. PATENT DOCUMENTS

| 4,987,898 | A | | 1/1991 | Sones | |
|---|---|---|---|---|---|
| 6,213,943 | B1 | * | 4/2001 | Abreu | 600/405 |
| 6,440,070 | B2 | * | 8/2002 | Israel | 600/398 |
| 6,443,893 | B1 | * | 9/2002 | Schnakenberg et al. | 600/398 |
| 6,447,449 | B1 | * | 9/2002 | Fleischman et al. | 600/405 |
| 2002/0099359 | A1 | * | 7/2002 | Santini et al. | 604/521 |
| 2002/0151816 | A1 | * | 10/2002 | Rich et al. | 600/547 |

FOREIGN PATENT DOCUMENTS

| DE | 3421701 A1 | 12/1984 |
|---|---|---|
| WO | WO 00/71982 A1 | 11/2000 |

* cited by examiner

*Primary Examiner*—Charles Marmor
(74) *Attorney, Agent, or Firm*—Oliff & Berridge, PLC

(57) ABSTRACT

Proposed is a device and a method for determining the inner pressure of a human eye, in which a plurality of pressure sensing elements, placeable on the eye, are used for measurement, with spatial resolution, of pressure values, which pressure-sensing elements are preferably disposed in a pressure sensor array, in particular in a microelectromechanical pressure sensor array with at least one line of pressure sensing elements. The intraocular pressure is determined from the sum of the measured sensor pressure values and the number of pressure-sensing elements contributing to the sum. Pressure distribution profiles with spatial resolution and pressure distribution matrices are able to be shown graphically.

25 Claims, 2 Drawing Sheets

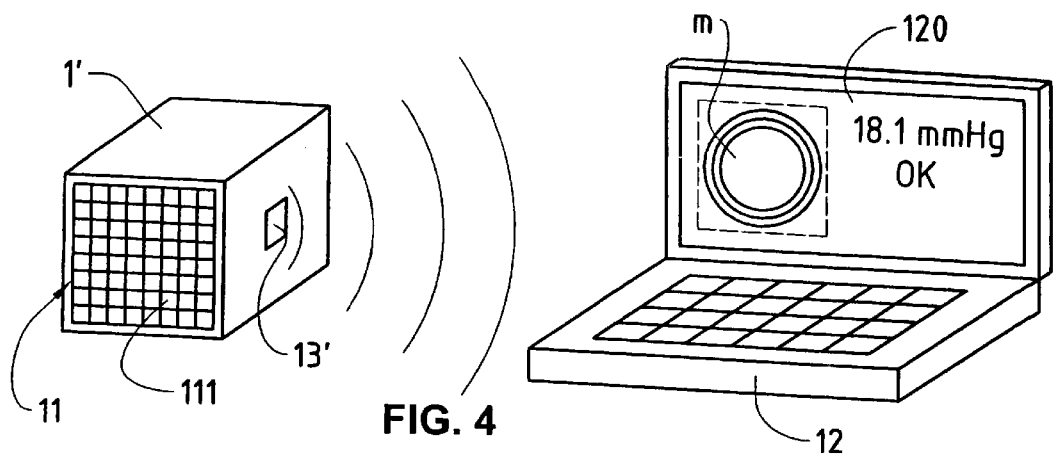
FIG. 4
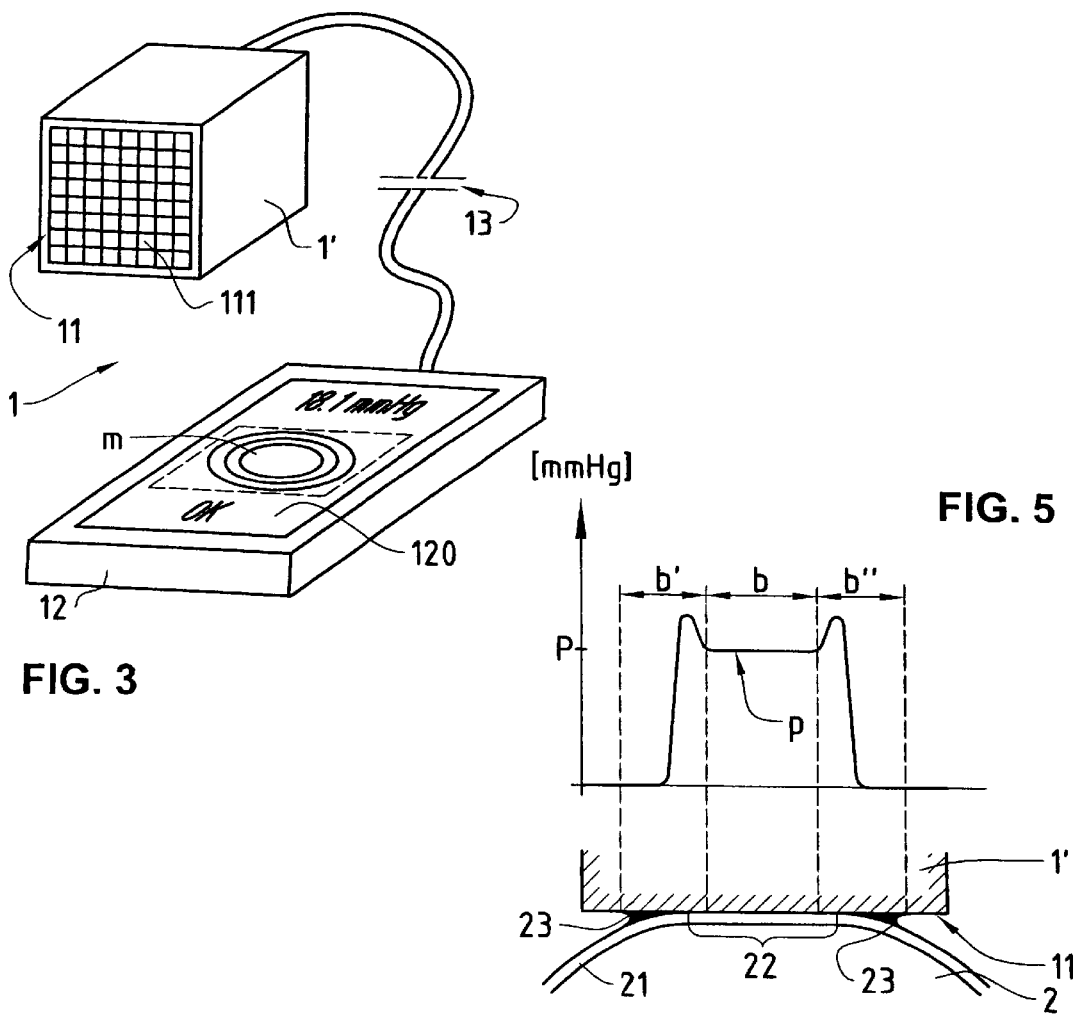
FIG. 3
FIG. 5

DEVICES AND METHODS FOR DETERMINING THE INNER PRESSURE OF AN EYE

This invention relates to devices and methods for determining the inner pressure of an eye. More specifically, this invention relates to a device and a method for determining the inner pressure of a human eye and a measuring sensor for capturing measurement values for determining the inner pressure of a human eye.

The inner pressure of the eye or so-called intraocular pressure (IOP) is maintained through a regulated flow of water in the eye chamber. In ophthalmology, the measurement of the intraocular pressure is of great importance for medical diagnosis. Too low an intraocular pressure leads to destabilization of the eye. Too high an intraocular pressure can lead to glaucoma, a very diverse group of diseases of the eye in which the IOP is too high for a normal, lasting functioning of the optic disk. The intraocular pressure is considered at the present time to be the most important and most easily measured parameter in the treatment and early diagnosis of glaucoma. Statistical records show, for example, an average intraocular pressure of 15.9 mm Hg (1 mm Hg=1.33 mbar) for men and 16.6 mm Hg for women. The intraocular pressure is subject both to daily fluctuations of 3 to 6 mm Hg and to fluctuations through blood pressure (pulse) of about 1.5 mm Hg. Although the intraocular pressure differs from individual to individual, 21 mm Hg is often set as the limit value at which at least further medical clarification of glaucoma risk is considered necessary. Furthermore a daily fluctuation of the IOP by 10 mm Hg is considered pathological. In the latest approaches, even a change in the brief fluctuations of the IOP caused by the pulse are examined for glaucoma.

The intraocular pressure is measured by so-called tonometers. In the known tonometry methods, the pressure is determined through measurement of force with known area or through measurement of area with known force. There are also tonometry methods in which an external pressure is applied to the eye and the applied pressure is measured. In addition, there are non-contacting tonometers which generate a flattening of the cornea by means of an air blast, and the IOP is thereby able to be measured. The most widespread tonometer at the present time and the one considered to be the most precise, the Goldmann applanation tonometer, is based on a force measurement with constant contact surface area (with flat contacting, this is referred to as the applanation surface). With Goldmann applanation tonometers, the size of the applanation surface is selected such that the forces caused by the cornea stiffness and the adhesion forces, caused by the meniscus of the tear fluid between the applanation surface and the eye, offset one another, which is the case for circular applanation surfaces having a diameter of 3 to 4 mm. With Goldmann applanation tonometers, the predefined size of the applanation surface is set by increasing the force applied to the applanation surface until two semicircles touch when looking through the transparent applanation element provided with a double prism. The intraocular pressure IOP then results from the ratio F/A of the measured force F applied to the applanation surface and the set predefined applanation surface area A. Goldmann applanation tonometers are used with a slit lamp, and are typically designed as standing apparatus so that the patient has to be seated, and self tonometry, performed by the patient himself, is not possible. Hand-held embodiments of the Goldmann applanation tonometer are achieved in a way still more costly with respect to the technology of the device.

The technical investment with respect to apparatus is very high with the Goldmann applanation tonometer, above all if the measurement process is automated, as is necessary for self-tonometry by the patient, since the applanation surface area has to be determined and set automatically.

Described in the published patent application WO 00/71982 is a newer device for determination of the intraocular pressure which is designed as a simple-to-insert contact lens and which therefore seems that it could be suitable for self-tonometry by the patient. The contact lens according to WO 00/71982 has a concave recess whose surface contour is adapted to the curvature of the human eye. A bore, sealed by a membrane, is provided at the vertex of the recess. The bore is part of a fluid-filled chamber system which transmits to a pressure measuring unit, located in the chamber system, a pressure exerted on the membrane, the fluid serving as a pressure transmission medium. Owing to the shape of the device according to WO 00/71982, the intraocular pressure can be greatly influenced, however, by a placement on the eye not according to directions (gently and with no application of force) and by periodic lifting of the device from the eye so that measurement values result indicating an incorrect IOP. This definitely makes self-tonometry by the patient more difficult.

To obtain a correct measurement result, the known tonometers must be applied very precisely, in particular perpendicular to the cornea, and carefully. Moreover, since some of the known tonometers only indicate the momentary value of the IOP, several measurements need to be carried out to determine the average IOP. Furthermore the known tonometers, when compared to one another, give differing measurement results. The thickness, the stiffness and the shape of the cornea influence the measurement results for the IOP in many methods. To take into consideration the corneal thickness, attempts are being made, among other things, to combine the IOP measurement with a measurement of the corneal thickness.

It is an object of this invention to propose a device and a method for determining the inner pressure of the eye, which device does not have at least certain of the above-described drawbacks of the state of the art and which makes possible, in particular, determination of the intraocular pressure with spatial resolution.

In particular, these objects are achieved in that the device for determining the intraocular pressure comprises a plurality of pressure-sensing elements that are placed directly or indirectly on the eye, and it comprises processing means for determining the intraocular pressure from the sensor pressure values measured by the individual pressure-sensing elements. The pressure-sensing elements are preferably disposed in a pressure sensor array which is placed directly or indirectly on the eye, the pressure sensor array comprising at least one line, but preferably a plurality of lines, of pressure-sensing elements. The advantage of using a plurality of pressure-sensing elements, in particular a pressure sensor array, for determining the intraocular pressure is above all that the intraocular pressure can be determined with spatial resolution. Irregularities in the local pressure distribution can thereby be recognized, and, for example, a poor application, i.e. an incorrect placement of the pressure sensor array on the eye, can be recognized as an invalid measurement. In particular, too forceful or too weak contacting (in the case of planar contacting, this is called applanation) of the eye during placement of the pressure sensor array can be recognized and can be indicated to the user. Since neither a predefined size of the contact surface (applanation surface in the case of planar contacting) nor a predefined pressing force has to be set, patients also need to be positioned less still and aligned. Moreover, in the case of a flat arrangement of the pressure-sensing elements, an especially simple application of the device is made possible since only a flat surface (pressure sensor array) has to be brought into contact with a spherical section (cornea), and special attention does not have to be paid to a centering of the contact surface and to a perpendicular application of the device, as with some state-of-the-art methods. A further advantage is that use of a pressure sensor array makes possible determination of the intraocular pressure without moving mechanical parts.

The processing means are preferably designed such that they determine the inner pressure of the eye from the sum of the measured, and e.g. weighted, sensor pressure values and the number of pressure-sensing elements contributing to the sum. Since the intraocular pressure is calculated through a division of the sum of the measured sensor pressure values by the number of contributing (active) pressure-sensing elements, the pressure sensor array does not have to rest on the eye with all its pressure-sensing elements. From this results the advantage that different contact conditions are suitable for determining the intraocular pressure, and, for example, oval contact surfaces, such as arise with astigmatism, do not falsify the determination of the intraocular pressure.

In an embodiment variant, the device comprises filter means to exclude, according to predefined criteria, certain measured sensor pressure values from the summation. Individual sensor pressure values which unfavorably influence the calculation of the intraocular pressure can thereby be excluded from the determination of the inner pressure of the eye. For example, sensor pressure values that are measured by pressure-sensing elements on the outer edge of the contact area and that are influenced by the stiffness of the cornea and/or by the adhesion forces of the lacrimal meniscus between the eye and the respective pressure sensor element, can be excluded from the determination of the intraocular pressure. Sensor pressure values can also be excluded that would otherwise falsify the determination of the intraocular pressure owing to variable corneal thickness of the respective eye, as a result of local corneal thickening or depression, for instance. It is also possible to detect irregularities caused by the corneal stiffness and to use them to compensate for the influences of the corneal stiffness. The exclusion of certain measured sensor pressure values can be also advantageous when the pressure sensor array used has a coarse spatial resolution, i.e. when the pressure sensor array is made up of few pressure-sensing elements which each measure a relatively large contact surface, so that individual pressure sensor elements on the outer edge of the contact area rest only partially on the eye.

In an embodiment variant, the device comprises memory means for storing of the measured sensor pressure values and for storing a multiplicity of certain values of the inner pressure of the eye. The capturing (measuring) of the sensor pressure values and the evaluation of the captured sensor pressure values can thereby be carried out in different steps, shifted with respect to time, which can also facilitate self-tonometry by the patient, for example. The storing of the measured sensor pressure values also makes calculation easier of the temporal averages for the measured sensor pressure values. Moreover the amplitude of the pressure fluctuation of the IOP caused by the pulse of the blood pressure can also be recorded. The storing of a multiplicity of particular inner pressure values for the eye, each preferably together with associated time indications, makes possible moreover the comparison of intraocular pressure values taken at different times.

In an embodiment variant, the device comprises representation means for graphic illustration and in particular depiction with spatial resolution of the measured and/or stored sensor pressure values. Pressure distribution profiles along a line through the contact surface and/or two-dimensional pressure distribution profiles over the entire contact surface, e.g. pressure distribution matrices, can thereby be shown and analyzed. By means of the sensor pressure values stored through graphic representation, sequences of pressure distribution profiles and pressure distribution matrices can also be shown and analyzed.

In an embodiment variant, the device comprises communications means for remote transmission of the determined inner pressure values for the eye. It is thereby made possible, for example, for the inner pressure values for the eye determined by a patient through self-tonometry to be transmitted to a responsible physician for recording and evaluation.

The pressure sensor array is preferably designed as a micro-electromechanical system (MEMS). A high degree of integration and thus a high degree of miniaturization are thereby made possible so that compact, portable devices can be achieved with a high spatial resolution.

In an embodiment variant, the pressure sensor array is incorporated into a measuring sensor that is connected to an evaluation unit via an interface having contacts or a contactless interface. Especially compact measuring sensors can thereby be achieved which can be combined via corresponding interfaces and programmed software modules with conventional processing and display units, for instance with palmtop, laptop or personal computers or with mobile radio telephones.

An embodiment of the present invention will be described in the following with reference to an example. The example of the embodiment is illustrated by the following attached figures:

FIG. 3 shows a schematic depiction of a further embodiment variant of the device for determining the intraocular pressure in which the measuring sensor is connected to an evaluation unit via an interface having contacts.

FIG. 4 shows a schematic depiction of a device configuration for determining the intraocular pressure in which the measuring sensor is connected to the evaluation unit via a contactless interface.

FIG. 5 shows a schematic example of a pressure distribution profile along a line through the surface on which the measuring sensor rests on the eye (i.e. through the contact surface, or, in the case of planar contact, through the applanation surface).

Figure 1:
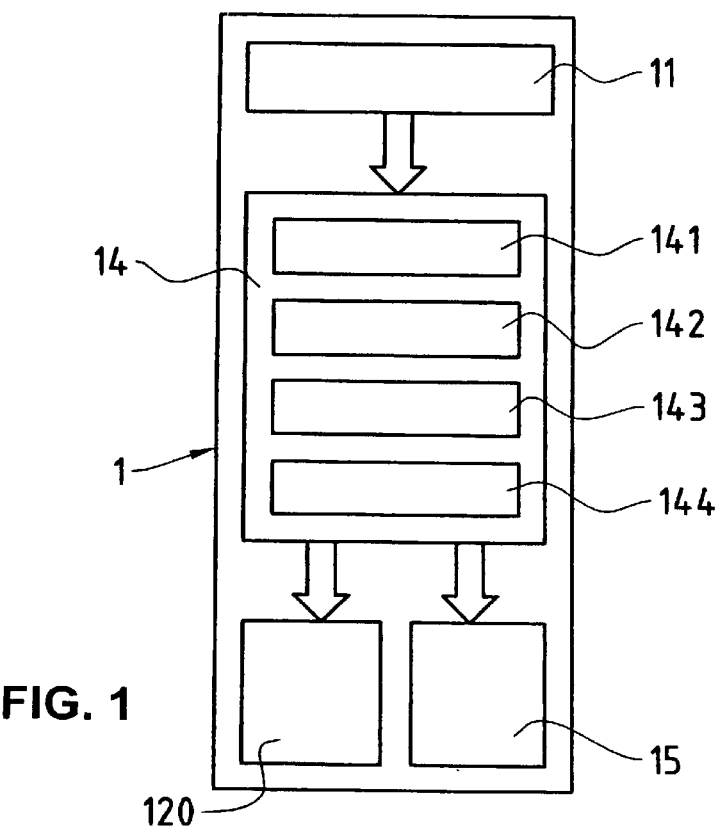
FIG. 1 shows a block diagram illustrating schematically a device for determining the intraocular pressure with a pressure sensor array, processing means and a display.

The reference numeral 1 in FIG. 1 designates the device for determining the intraocular pressure, which is also referred to as the measuring device 1 in the following text. The measuring device 1 comprises a plurality of pressure-sensing elements 111, which are disposed, for instance, in a pressure sensor array 11, e.g. along a line, a straight line or a circular line, but preferably matrix-shaped. The pressure-sensing elements 111 can also be executed as pressure-sensing rings and arranged concentrically. Pressures, which are picked up by the pressure-sensing elements 111, lead to deformation of sensitive elements of the pressure-sensing elements 111, which are detected e.g. capacitively, piezoelectrically, resistively, optically, through changes in resonance frequencies or through other suitable methods, depending upon embodiment of the pressure-sensing elements 111, or respectively of their sensitive elements. The sensitive elements of the pressure-sensing elements 111, by means of which the pressure is detected, are placed on the cornea 21 or the sclera of the eye 2, directly over sensor surfaces, for instance. It is also possible, however, for the sensor surfaces to be connected to the sensitive elements of the pressure-sensing elements 111 via suitable connections, for example fluid connections. Fluid connections can be of a static or dynamic nature. With dynamic connections, for instance, an air current or liquid current is conveyed to an aperture that is in direct or indirect contact with the cornea. With the approach to, and contact with, the cornea, the current resistance is increased at the aperture. The arising counter-pressure at the cornea can be used for measuring the IOP.

It should be stressed here that the placement of the pressure-sensing elements 111, or respectively of the pressure sensor array 11, on the eye 2 can take place directly or indirectly. Besides determining the intraocular pressure through direct placement of the pressure sensor array 11 on the eye 2, determination of the intraocular pressure can also be carried out through placement of the pressure sensor array 11, or respectively of the pressure-sensing elements 111, on a contact lens put on the cornea 21 or through placement on the closed eyelid. Determination of the intraocular pressure through a contact lens or an eyelid has the advantage that the eye is not harmed by contact with the pressure-sensing elements 111.

The pressure sensor array 11 is preferably executed as a micro-electromechanical system. Micro-electromechanical pressure sensor arrays 11 are available which are integrated on a chip together with processing units, for instance with analog/digital converters for digitalization of measurement values. Such pressure sensor array chips are produced, for example, by means of CMOS-compatible process techniques. Pressure sensor arrays are developed and used particularly in the field of tactile sensing, for instance in robotics. Further applications of pressure sensor arrays are to be found in biometry, e.g. in the recognition of fingerprints or in the measurement of pressure profiles on foot sole treading surfaces. Produced by Toyota, for example, in CMOS technology, is a pressure sensor array chip with 32×32 pressure-sensing elements 111, a lateral resolution of 250 $\mu$m and a total size of 10×10 mm. As will be described later with reference to FIGS. 2 to 5, the pressure sensor array 11 for placement on the eye 2 is incorporated into a measuring sensor 1'. To obtain sterile measuring conditions and to protect the eye and the pressure sensor array 11, the pressure sensor array 11 is covered, for example, by means of a disposable membrane. One skilled in the art will understand that the pressure sensor array 11 can be executed with just one single line of pressure-sensing elements 111. It is also conceivable, however, to dispose the pressure-sensing elements 111 of the pressure sensor array 11 not flat, but instead on a curved carrier whose contour is adapted, for instance, to the curvature of the human eye. The pressure-sending elements 111 are preferably disposed regularly in the pressure sensor array 11; the spacing between the individual pressure-sensing elements 111 can also differ, however.

As is shown schematically in FIG. 1, the pressure sensor values measured by the pressure-sensing elements 111 of the pressure sensor array 11 are passed on to the processing means 14 for further evaluation. If pressure sensor arrays 11 are used containing pressure-sensing elements 111 that also pick up shearing forces, in addition to normal forces, measured shearing forces (transverse forces) can also be conveyed to the processing means 14, in addition to the measured pressure sensor values, for evaluation.

The processing means 14 include memory means 141, in particular electronic data stores, in which the measured pressure sensor values are stored. The memory means 141 comprise, for instance, electronic data stores that are integrated on a chip together with the pressure sensor array 11.

The processing means 14 comprise filter means 142, which exclude, according to predefined criteria, certain of the measured pressure sensor values from further processing. Excluded from further processing are in particular pressure sensor values that would falsify the determination of the intraocular pressure. The filter means 142 are executed either as hardware, for instance as integrated circuits, or as programmed software modules for control of a processor. The way of functioning of the filter means 142 corresponds to known algorithms from digital signal and image processing, the matrix or line of measured sensor pressure values corresponding—in analogy to image processing—to a picture matrix or picture line of pixels (picture element) with digitalized gray scale values. Available are DSP (Digital Signal Processor) chips, programmable for any desired purpose, or picture processing processor chips, as well as processing algorithms integrated into chips.

One of the functions of the filter means 142 should be explained with reference to FIG. 5. Indicated schematically in the lower portion of FIG. 5 is a measuring sensor 1' which, with its sensor array 11, is situated on the cornea 21 of an eye 2. The surface on which the sensor array 11 rests on the cornea 21, the contact surface (or applanation surface, with planar placement), is designated by the reference numeral 22 in FIG. 5. Shown, as an example, in the upper portion of FIG. 5 is a pressure distribution profile p which corresponds to the course of the captured pressure values along a line through the contact surface 22 or along a line of the pressure sensor array 11 resting on the eye 2. The regions of the pressure distribution profile p designated by b' and b" comprise sensor pressure values measured by those pressure-sensing elements 111 of the pressure sensor array 11 that are under the influence of the corneal stiffness and/or under the influence of the adhesion forces caused by the lacrimal meniscus 23 situated between the cornea 21 and the pressure sensor array 11. The pressure-sensing elements 111 influenced by the meniscus of tear fluid 23 are situated in an area outside the contact surface 22. The region of the pressure distribution profile p designated by b comprises the sensor pressure values measured by those pressure-sensing elements 111 of the pressure sensor array 11 resting in the inner region of the contact area 22 and which are only slightly, or not at all, influenced by the corneal stiffness and/or the lacrimal meniscus 23. Since the regions b' and b" of the pressure distribution profile p could falsify the calculation of the intraocular pressure based on the measured sensor pressure values, the sensor pressure values situated in these regions could be excluded by the filter means 142 from further processing. The corresponding filter function can be achieved, for example, through filtering of the sensor pressure values which are above, or respectively below, the sensor pressure value P prevailing in the region b at least by a defined difference value. The respective filter function can also be achieved through filtering of the sensor pressure values that are captured within a predefined or dynamically determined geometric area b. Corresponding filter functions can also be used for the exclusion of sensor pressure values measured by pressure-sensing elements 111 located in the outer region of the contact surface 22 and lying only partially on the cornea 21. A partial lying of pressure-sensing elements 111 is possible, for instance, with pressure sensor arrays 11 having coarse spatial resolution, whose pressure-sensing elements 111 have an element width of one millimeter or more than one millimeter.

The filter means 142 can also include functions excluding measured sensor pressure values which would otherwise falsify the calculation of the intraocular pressure owing to variable corneal thickness of the respective eye 2, for instance as a result of local corneal thickening or depression, caused e.g. by operative procedures. Moreover it can be advantageous if at least certain filter functions of the filter means 142 are able to be alternatively switched on or off by the user. The filter means 142 can also be executed in such a way that they make it possible for the user to set and to select areas of interest.

The processing means 14 include pressure calculation means 143 which calculate the inner pressure of the eye from those measured sensor pressure values not excluded by the filter means 142. The sum of these sensor pressure values, which are e.g. weighted, are thereby divided by the number of pressure-sensing elements 111 contributing to the sum, i.e. the number of active pressure-sensing elements 111 which indicate a measured sensor pressure value and whose sensor pressure value has not been excluded by the filter means 142 from further processing. The pressure calculation means 143 are executed either as hardware, for instance as integrated circuits, or as programmed software modules for control of a processor. For calibration of the measured sensor pressure values in standardized pressure values, the processing means 14 include moreover calibration functions, and, depending upon the embodiment, also calibration tables belonging thereto. The processing means 14 also comprise, for instance, a calibration function which makes it possible for the user to calibrate the pressure-sensing elements 111 in alternative ways, e.g. a calibration can be selected that delivers measuring values corresponding to those of a Goldmann applanation tonometer.

The processing means 14 include representation means 144 for graphic depiction of the measured sensor pressure values on a display 120, for instance an LCD display. The representation means 144 are preferably executed as programmed software modules for control of a processor. The representation means 144 include, for instance, functions for generating and representing pressure distribution profiles p according to FIG. 5, or two-dimensional pressure distribution profiles m (with multiple-line pressure sensor arrays 11), which represent the two-dimensional pressure profile of the pressure sensor array 11. The two-dimensional pressure distribution profiles m are, for example, pressure distribution matrices in which the matrix of the measured sensor pressure values are imaged with spatial resolution, for instance by means of differing gray or color tones corresponding to the sensor pressure values (see FIGS. 3 and 4). The resolution and the representation of the two-dimensional pressure distribution profiles m need not coincide with the number of pressure sensor elements 111 and/or the structure of the pressure sensor array 11, however. The representation means 144 also include, for example, functions for graphic depiction of the temporal course of the calculated intraocular pressure or for graphic presentation of sequences of captured and/or stored lines or matrices of measured sensor pressure values. The representation means 144 can also be combined with the filter means 142, for instance, such that, alternatively, sensor pressure values excluded by the filter means 142 from the calculation of the intraocular pressure can be taken into consideration, and emphasized optically, for instance, in the representation of the pressure distribution profiles p, m (pressure distribution matrices). In this way, for instance, irregularities of the eye, e.g. variable-thickness of the cornea, can also be made visible on the display 120.

For purposes of operation and control, the measuring device 1 includes moreover operating elements, for instance keys, by means of which it is possible to use menus also shown on the display 120, for instance.

The measuring device 1 can also be operated in different operating modes that can be selected by the user. In a first operating mode, the sensor pressure values measured by the pressure-sensing elements 111 of the pressure sensor array 11 are captured, are stored in the memory means 141, and the intraocular pressure is calculated directly therefrom and is shown on the display 120, for instance together with the corresponding pressure distribution profile p, m (e.g. a pressure distribution matrix). In a further operating mode, multiple sequential determination of the intraocular pressure according to the first operating mode is carried out automatically, and the average is displayed as the resulting intraocular pressure. In still a further operating mode, the sensor pressure values measured by the pressure-sensing elements 111 of the pressure sensor array 11 are captured continuously, are stored in the memory means 141, and the current and/or average intraocular pressure is calculated directly therefrom and is displayed on the display 120, for example together with the temporal course of the intraocular pressure. In this way pressure fluctuations, caused by the pulse of the blood pressure, can also be made visible, for example. In particular, to aid the user during use of the measuring device 1, the pressure distribution profile p, m (e.g. a pressure distribution matrix) of the continuously measured current sensor pressure values can be displayed on the display 120, for instance without interim storage in the memory means 141, so that the user obtains real-time feedback of the contact (applanation) generated through the placement of the pressure sensor array 11 on the eye 2. A correct application can be indicated to the user (OK), for example, and the possibility given to him of activating the measurement according to a selected operating mode, for instance by pressing a button.

The calculated values for the intraocular pressure can be stored in the memory means 141 also long-term, for instance automatically or alternatively, upon command of the user. Calculated and stored values can be compared to one another, and can be conveyed to a physician, for instance. For later evaluation, the calculated values for the intraocular pressure are stored in the memory means 141, preferably together with time indications about the time of the intraocular pressure taking, for instance comprising clock time and date, and supplied by a time recording module (not shown) of the device 1. In addition, further information associated with the pressure values for the eye can be stored in the memory means 141, for example indications about measuring conditions, the state of the patient, or medicines taken by the patient. This supplementary information can be entered, for instance, by means of spoken language or by means of the operating elements mentioned above. For transmission of the calculated values for the intraocular pressure, the device 1 includes, for example, a communications module 15 which is designed e.g. for data transmission via mobile radio networks 15, for instance GSM (Global System for Mobile Communication) or UMTS networks (Universal Mobile Telephone System), or fixed networks, for example PSTN (Public Switched Telephone Network), ISDN (Integrated Services Digital Network) or IP networks (Internet Protocol). Stored values can be erased upon command of the user and/or automatically, for instance after a predefined time period.

Figure 2:
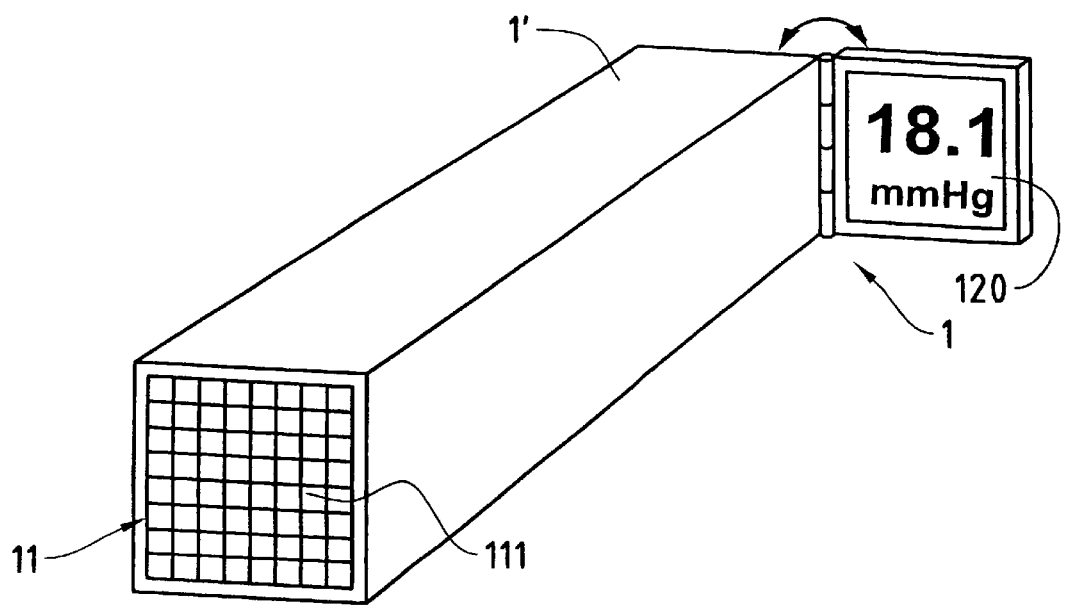
FIG. 2 shows a schematic depiction of the device for determining the intraocular pressure in which the measuring sensor with the pressure sensor array is provided with a display.

Shown schematically in FIG. 2 is a compact embodiment variant of the measuring device 1, which is especially well suited to self-tonometry by the patient. In this embodiment variant, the entire measuring device 1 with the pressure sensor array 11 and the processing means 14, for example battery-fed, is accommodated in a mobile, portable measuring sensor 1', the display 120 being disposed such that it can be read by the examining physician or by the patient himself, in that it is designed pivotable, for instance, as illustrated in FIG. 2.

Shown schematically in FIG. 3 is an embodiment variant of the measuring device 1 in which the functional modules of the measuring device 1 are distributed on the measuring sensor 1' and the evaluation unit 12. As shown in FIG. 3, the measuring sensor 1', comprising the pressure sensor array 11, is connected to the evaluation unit 12, comprising the display, via an interface 13 having contacts, for example a cable connection with a feeding line. The processing means 14 can be distributed in various ways on the measuring sensor 1' and the evaluation unit 12. In addition to the pressure sensor array 11, the measuring sensor 1' includes, for instance, memory means 141 for storing at least one matrix or one line of measured sensor pressure values. Further memory means 141 for storing further matrices, the filter means 142, the pressure calculation means 143 and the representation means 144 are disposed, for instance, in the evaluation unit 12, which comprises a programmable processor, for example.

Shown schematically in FIG. 4 is an embodiment variant of the measuring device 1 in which the measuring sensor 1', that is designed substantially as in the embodiment variant according to FIG. 3, and the evaluation unit 12 are connected to one another via a contactless interface 13', for instance an infrared or radio interface. The evaluation unit 12 is, for example, a conventional palmtop or laptop computer additionally provided with a contactless interface 13'. The filter means 142, the pressure calculation means 143 and the representation means 144 are executed, for example, as programmed software modules in the evaluation unit 12.

The proposed measuring device 1 or the proposed measuring device 1' makes possible measurement of the intraocular pressure through simple application of a plurality of pressure-sensing elements 111, without a force or a surface area having to be set precisely, it being possible to record a pressure profile continuously.

What is claimed is:

1. A device for determining intraocular pressure, comprising:
    a plurality of pressure-sensing elements; and
    processing means for determining the intraocular pressure from a sum of the sensor pressure values measured by the individual pressure-sensing elements and from a number of the pressure-sensing elements contributing to the sum.

2. The device according to claim 1, further comprising a pressure sensor array with at least one line of the pressure-sensing elements.

3. The device according to claim 2, wherein the pressure sensor array is designed as a micro-electromechanical system.

4. The device according to claim 2, wherein the pressure sensor array is incorporated into a measuring sensor which is connected to an evaluation unit via an interface with contacts.

5. The device according to claim 2, wherein the pressure sensor array is incorporated into a measuring sensor which is connected to an evaluation unit via an interface without contacts.

6. The device according to claim 2, further comprising filter means for excluding those measured sensor pressure values from the sum which are above a sensor pressure value at least by a defined difference value, said latter sensor pressure value being measured by those pressure-sensing elements resting in an inner region of a contact area on which the sensor array rests directly or indirectly on an eye in an applied state of the device.

7. The device according to claim 1, wherein the processing means are designed to determine the intraocular pressure from the sum of measured and weighted sensor pressure values and from the number of the pressure-sensing elements contributing to the sum.

8. The device according to claim 7, further comprising filter means for excluding, according to predefined criteria, certain measured sensor pressure values from the sum.

9. The device according to claim 1, further comprising memory means for storing the sensor pressure values and for storing a plurality of particular values for the intraocular pressure.

10. The device according to claim 9, further comprising representation means for graphically representing the at least one of measured and stored sensor pressure values, and intraocular pressure values.

11. The device according to claim 1, further comprising communications means for remotely transmitting the determined intraocular pressure values.

12. The device according to claim 1, wherein the device is a compact, mobile, portable device.

13. A system for determining intraocular pressure, comprising:
    a measuring sensor for capturing measurement values for determining the intraocular pressure,
    comprising a plurality of pressure-sensing elements and an evaluation unit, comprising processing means for determining the intraocular pressure from the sum of the sensor pressure values measured by individual pressure-sensing elements and from the number of the pressure-sensing elements contributing to the sum; and
    an interface for transmission of the sensor pressure values, measured by the individual pressure-sensing elements, to the evaluation unit.

14. The system according to claim 13, wherein the measuring sensor further comprises a pressure sensor array with at least one line of pressure-sensing elements.

15. The system according to claim 14, wherein the interface comprises contacts.

16. The system according to claim 14, wherein the interface is contact-less.

17. The system according to claim 13, wherein the interface comprises contacts.

18. The system according to claim 13, wherein the interface is contact-less.
    determining the intraocular pressure from a sum of the sensor pressure values measured by the individual pressure-sensing elements and from a number of the pressure-sensing elements contributing to the sum.

19. The system according to claim 13, wherein the evaluation unit further comprises filter means for excluding those measured sensor pressure values from the sum which are above a sensor pressure value at least by a defined difference value, said latter sensor pressure value being measured by those pressure-sensing elements resting in an inner region of a contact area on which the measuring sensor rests directly or indirectly on an eye in an applied state of the measuring sensor.

20. A method for determining intraocular pressure, comprising:

at least one of placing directly and indirectly, a plurality of pressure-sensing elements on an eye; and determining the intraocular pressure from a sum of the sensor pressure values measured by the individual pressure-sensing elements from a number of the pressure-sensing elements contributing to the sum.

21. The method according to claim 20, wherein a pressure sensor array with at least one line of pressure-sensing elements is placed on the eye.

22. The method device according to claim 21, wherein those measured sensor pressure values are excluded from the sum in which are above a sensor pressure value at least by a defined difference value, said latter sensor pressure value being measured by those pressure-sensing elements resting in an inner region of a contact area on which the sensor array rests directly or indirectly on the eye.

23. The method according to claim 13, wherein the intraocular pressure is determined from the sum of measured and weighted pressure values and from the number of pressure-sensing elements contributing to the sum.

24. The method according to claim 23, wherein certain measured sensor pressure values are excluded, according to predefined criteria, from the summation.

25. The method according to claim 20, wherein the pressure-sensing elements are placed on a contact lens placed on the eye or on the eyelid of the eye.

* * * * *